United States Patent

Norcross, Jr.

[11] Patent Number: 5,202,092
[45] Date of Patent: Apr. 13, 1993

[54] DEVICE FOR MONITORING THE PH OF WATER BASED INKS

[75] Inventor: Robert A. Norcross, Jr., Newton, Mass.

[73] Assignee: Norcross Corporation, Newton, Mass.

[21] Appl. No.: 801,889

[22] Filed: Dec. 3, 1991

[51] Int. Cl.$^5$ .................. G01N 21/00; G01N 27/416; G01N 27/26

[52] U.S. Cl. .................. 422/62; 422/82.04; 324/438; 204/433

[58] Field of Search .............. 422/62, 82.04; 324/438; 204/433

[56] References Cited

U.S. PATENT DOCUMENTS

| | | | |
|---|---|---|---|
| 3,899,294 | 9/1975 | Magiros | 23/230 A |
| 4,151,255 | 4/1979 | Capuano et al. | 422/76 |
| 4,239,493 | 12/1980 | Niemi et al. | 23/230 A |
| 4,329,649 | 5/1982 | Scoates | 324/438 |
| 4,415,858 | 11/1983 | Hale | 324/438 |
| 4,447,775 | 5/1984 | Breuker et al. | 324/438 |
| 4,609,874 | 9/1986 | Reich | 324/438 |
| 4,762,796 | 8/1988 | Weber et al. | 436/55 |

FOREIGN PATENT DOCUMENTS

0413232A2 7/1990 European Pat. Off. .
3812108A1 12/1988 Fed. Rep. of Germany .
599001 1/1944 United Kingdom .

Primary Examiner—James C. Housel
Assistant Examiner—N. Bhat
Attorney, Agent, or Firm—Robert F. O'Connell

[57] ABSTRACT

A device for automatically and continually monitoring the pH characteristic of a water based printing ink which uses a housing for a pH probe, which housing is placed in a flow line through which such ink is flowing, the housing having a main channel for ink flow and a recessed channel into which a pH probe member is inserted. A baffle is provided to direct a portion the flowing ink into the recessed channel in contact with the probe to continually monitor the pH of the flowing ink. A portion of the ink remains in the recessed channel when ink flow is stopped so that the probe surface is covered by the remaining ink and cannot dry out and reduce or destroy the effectiveness of the probe.

5 Claims, 1 Drawing Sheet

DEVICE FOR MONITORING THE PH OF WATER BASED INKS

This invention relates generally to techniques for monitoring characteristics of printing inks and, more particularly, to a novel device for monitoring the pH characteristics of water based printing inks.

BACKGROUND OF THE INVENTION

The continued monitoring of pH characteristics of water-based printing inks has become an important factor when using such inks in printing systems and it is desirable that effective techniques be devised for doing so automatically in a continual, in-line, manner. At the present time, monitoring the pH characteristics of inks in such printing systems is primarily done manually, usually by using a hand-held pH probe having a glass membrane surface which is inserted from time to time into the ink as it flows from an ink pump source to the printer.

Automatic pH probe techniques that have been proposed, in which the probe is merely inserted into the line to project into the flow path, tend to raise a problem in that, when the ink pump source is turned off, the ink flowing through the line in which the probe is located drains back into the pump source leaving the glass membrane surface of the probe exposed to air so that any residual undrained ink still present on portions of the probe surface tends to dry thereon. Over time as such activity occurs, the effectiveness of the probe is reduced or destroyed, by the pressure of such residual, dried ink (the probe is sometimes referred to as having been "poisoned") and the probe must then be replaced. Depending on how often the ink flow in the line is shut off, e.g., when the ink being used is temporarily not required or when a different color ink from that currently being used is required in the line so that a new ink source must be attached thereto, probe replacement may be required relatively often thereby raising the material and labor costs of the printing process.

It is desirable to provide an in-line pH probe monitoring device which automatically provides continued pH measurements, so long as ink flows in the line, and in which the need for frequent replacement of the probe is reduced, even when the flow of an ink is temporarily stopped for whatever reason.

BRIEF SUMMARY OF THE INVENTION

In accordance with a preferred, specific embodiment of the invention, a pH monitoring device includes a probe assembly having therein a chamber that is coupled at input and output ports thereof to a line through which a water based printing ink flows. The chamber includes a recessed channel at the bottom of the chamber into a portion of which a pH probe is inserted. A baffle member is positioned at the top of the chamber to project downwardly into the path of the ink flow so as to cause the incoming stream of ink flowing in the chamber to be diverted and directed downwardly into the recessed channel for contact with the glass membrane surface of the probe. A turbulent flow of ink occurs in the recessed channel, thereby effecting a combined scrubbing action at the exposed glass membrane surface of the probe. The ink thereupon flows out from the recessed channel to the outgoing side of the chamber and thence through the output port thereof.

When the ink pump source shuts down and no ink is then supplied therefrom, the ink still present in the chamber tends to flow back and be drained into the pump source. Because of the recessed channel, however, a portion of the ink is captured, or trapped, in the recessed channel above the exposed probe surface thereby forming a reservoir of ink at the probe surface which prevents such surface from being exposed to air. Enough ink is present on such surface so that there will be no drying or caking of ink thereat.

A further port is preferably provided in the baffle member and extends downwardly therethrough at a position opposite the recessed channel Such port is connected to a source of cleaning liquid, e.g., water, preferably under pressure, for directing a pressurized flow of cleaning liquid into the recessed channel to flush out the reservoir of ink that is present therein when the ink flow is stopped, for example, to permit a different color ink to be used for flow in the line. When the flushing operation is completed, the old ink has been flushed away and a reservoir of cleaning fluid remains in the recess above the probe to cover the exposed surface thereof to prevent any drying thereof. Such cleaning liquid reservoir is effectively carried away when a flow of different color ink begins.

BRIEF DESCRIPTION OF THE DRAWINGS

The invention can be described in more detail with the help of the accompanying drawings wherein.

DESCRIPTION OF THE INVENTION

Figure 1:
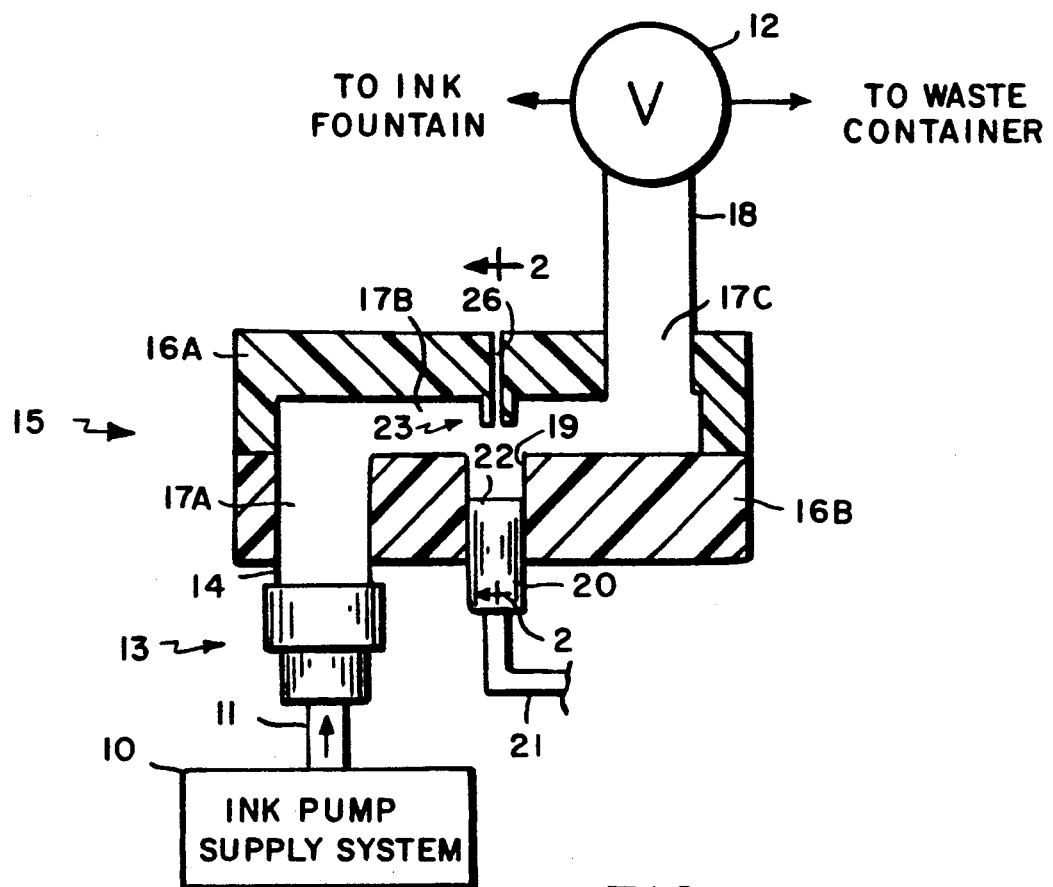
FIG. 1 shows a side view in section of a probe assembly in accordance with a preferred embodiment of the invention.
Figure 2:
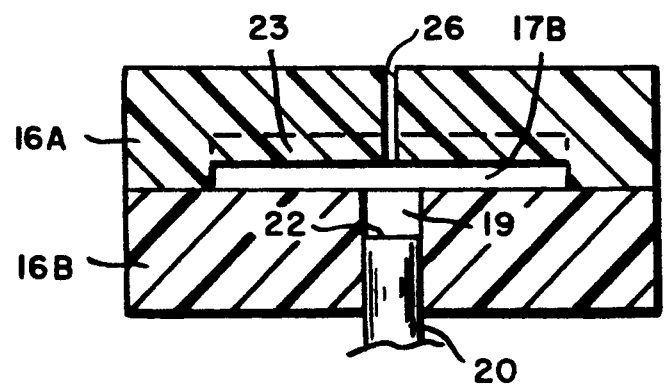
FIG. 2 shows an end view in section of a portion of the probe assembly along the line 2—2 of FIG. 1.

As can be seen in FIGS. 1 and 2, a flow of a water based printing ink is provided from an ink pump supply system 10 to an input line 11. The ink flowing therein is supplied via a coupling 13 to an input port 14 of an in-line pH probe assembly 15.

Probe assembly 15 includes a housing which is preferably formed of plastic and includes upper and lower snap-apart portions 16A and 16B, respectively. While the housing can be formed as a single integral piece, a snap-apart structure is helpful so that the overall assembly can be periodically and thoroughly cleaned. The probe assembly 15 contains a chamber therein which provides a main channel therein having an input channel portion 17A, a cross-channel portion 17B and an output channel portion 17C. The output channel portion is used to supply fluid, e.g., ink, for flow therefrom via output line 18 and a suitable valve 12 either to a conventional ink fountain assembly (not shown) or to a waste collection container or pail (not shown), for discard, as desired.

Housing portion 16B includes a recessed channel 19 into a portion of which a conventional pH probe member 20 can be inserted. Suitable leads 21 are connected to the probe for use in providing an output therefrom which represents the pH characteristic of a liquid which is in contact with the exposed surface 22 of probe member 20, in a manner well-known to those in the art.

A baffle member 23 extends across the inner surface of upper housing portion 16A at the top of main channel portion 17B. In a preferred embodiment, baffle member 23 extends about half-way down into main channel portion 17B and includes a cleaning port 26 formed therein and extending through baffle member 23 at a position opposite the recessed channel 19. A source of cleaning liquid (not shown) is connected to cleaning port 26.

During operation a water based printing ink is supplied from ink pump supply system 10 for flow through input line 11, main channel portions 17A, 17B, and 17C of the housing, and output line 18. A portion of the ink flowing therein is deflected, or diverted, downwardly by baffle member 23 so that such portion is directed into recessed channel 19 thereby filling the channel in contact with the exposed surface 22 of pH probe member 20 so that the pH characteristic of the ink can be continually monitored during a printing operation. The diversion of the ink stream by baffle member 23 causes a turbulent flow of ink to occur within recessed channel 19, the ink thereupon exiting channel 19 for flow toward the output line 18. Although the baffle means 23 is preferably shown as extending about half-way into the main channel, in some explications it may extend downwardly to a lesser or greater distance so long as it satisfactorily diverts a sufficient portion of the ink flow into the recessed channel and does not excessively interfere with the general flow rate of the ink through the main channel.

If the ink supply is temporarily shut-off so that no further ink flows through the probe assembly 15, the ink then present in the main channel thereof drains therefrom by flowing back to the ink pump supply system 10. The ink then present in recessed channel 19, however, remains therein and continues to cover the exposed surface of pH probe member 20 and thereby prevents exposure of such surface to air so as to avoid any drying or caking of ink thereon. Such a liquid protection layer at the probe surface prevents poisoning of the probe member and extends its useful life in the system. Ink flow can be subsequently resumed and the pH monitoring thereof can continue as before.

If ink flow is stopped, for example, in order to provide a different color ink for flow in the system, any residual amount of the previous color ink remaining in recessed channel 19 after ink flow has ceased can be cleared out before a new color ink is used by supplying a cleaning liquid, e.g., water, under relatively low pressure, e.g., 10 psi, or less, at cleaning port 26. The cleaning liquid is directed downwardly from port 26 into recessed channel 19 where a turbulent flow occurs for flushing the old ink therein, as well as the cleaning liquid, outwardly therefrom into output line 18 to a suitable waste discard container or back to the pump system 10 via input channel 17A. The cleaning liquid pressure may be more or less than 10 psi, or in some applications may even be operated merely as a gravity feed system, the flow thereof must be sufficient to assure a good cleaning action in the recessed channel. When the cleaning operation is completed and no further cleaning liquid is supplied at port 26, a portion of the cleaning liquid remains in recessed channel 19 to cover the exposed surface of probe member 20, again preventing such surface from being exposed to air. When ink flow operation is then resumed with a new, different color ink, the cleaning liquid in recessed channel 19 is automatically replaced with the new ink and the ink flow and printing operation resumes as before.

While the embodiment depicted in FIGS. 1 and 2 represents a preferred embodiment of the invention, modifications thereto may occur to those in the art within the spirit and scope of the invention. Hence, the invention is not to be construed as limited to the specific embodiment depicted therein, except as defined by the appended claims.

What is claimed is:

1. A device for automatically and continually monitoring the pH characteristic of a water based printing ink flowing through such device, said device comprising
    a pH probe housing assembly positioned in-line in a flow line through which a water based printing ink flows, said housing having an input port and an output port coupled to said flow line;
    a main channel formed in said housing between and in communication with said input and output ports so that said water based printing ink flows through said main channel;
    a recessed channel formed in said housing in communication with said main channel below the flow path of said main channel;
    means in said main channel for directing a first portion of said water based printing ink flowing through said main channel downwardly into said recessed channel, a second remaining portion thereof flowing directly through said main channel;
    a pH probe member inserted into said recessed channel, an exposed surface of said probe member being contacted by the first portion of said water based printing ink that is directed into said recessed channel for monitoring the pH characteristic of said ink, a residual portion of the ink flowing in said recessed channel remaining therein in contact with said exposed surface when the flow of ink through said housing is stopped.

2. A device in accordance with claim 1 wherein said directing means is a baffle means positioned in said main channel substantially opposite said recessed channel so as to extend only part way into said main channel in the flow path of ink flowing in said main channel.

3. A device in accordance with claim 2, wherein said baffle means is positioned so as to extend about half-way into said main channel.

4. A device in accordance with claim 3 and further including a cleaning port positioned in said baffle means for directing a cleaning liquid into said recessed channel when no ink is flowing through said housing to clean the exposed surface of said probe member, a portion of said cleaning liquid remaining in said recessed channel in contact with said exposed surface when said cleaning operation is stopped.

5. A device in accordance with claim 3, wherein said cleaning liquid is directed to said recessed channel at a pressure of about 10 psi.

* * * * *